(12) United States Patent
Engimann

(10) Patent No.: US 9,022,247 B2
(45) Date of Patent: May 5, 2015

(54) CONTAINER FOR DISINFECTION OF MEDICAL DEVICES

(71) Applicant: Cambridge Sensors USA LLC, Plainfield, IL (US)

(72) Inventor: Fredrick Engimann, Plainfield, IL (US)

(73) Assignee: Cambridge Sensors USA, LLC, Plainville, IL (US)

( * ) Notice: Subject to any disclaimer, the term of this patent is extended or adjusted under 35 U.S.C. 154(b) by 203 days.

(21) Appl. No.: 13/661,699

(22) Filed: Oct. 26, 2012

(65) Prior Publication Data
US 2013/0115132 A1   May 9, 2013

(30) Foreign Application Priority Data
Oct. 27, 2011 (GB) .................................. 1118588.1

(51) Int. Cl.
| | | |
|---|---|---|
| A47J 39/00 | (2006.01) |
| B65D 85/00 | (2006.01) |
| A61B 19/00 | (2006.01) |
| A61L 2/16 | (2006.01) |
| A61B 19/02 | (2006.01) |
| A61B 5/145 | (2006.01) |
| A61L 2/26 | (2006.01) |

(52) U.S. Cl.
CPC . *A61L 2/16* (2013.01); *A61B 19/02* (2013.01); *A61B 5/14532* (2013.01); *A61B 19/026* (2013.01); *A61B 19/0271* (2013.01); *A61L 2/26* (2013.01); *A61L 2202/182* (2013.01); *A61L 2202/24* (2013.01)

(58) Field of Classification Search
CPC .................................. A61L 2/00; A61L 2/18
USPC ................... 220/592.01; 422/1, 28, 292, 300; 206/459.1, 470; 604/403
See application file for complete search history.

(56) References Cited

U.S. PATENT DOCUMENTS 4,050,894 A * 9/1977 Genis ............................ 206/363

* cited by examiner

*Primary Examiner* — Monzer R Chorbaji
(74) *Attorney, Agent, or Firm* — Saliwanchik, Lloyd & Eisenschenk

(57) ABSTRACT

The present invention is directed to a container suitable for use in the disinfection of blood glucose meters and other medical devices. In one embodiment, the container comprises a tray with a formed cavity in it, such that a blood glucose meter or medical device may be placed and retained in it. In certain related embodiments, the meter has been wrapped in a disinfection wipe prior to placement into the container.

24 Claims, 3 Drawing Sheets

CONTAINER FOR DISINFECTION OF MEDICAL DEVICES

CROSS-REFERENCE TO A RELATED APPLICATION

This application claims priority to Great Britain Application No. 1118588.1, filed Oct. 27, 2011; which is incorporated herein by reference in its entirety.

FIELD OF THE INVENTION

The present invention relates to a container for disinfection of medical devices.

BACKGROUND OF THE INVENTION

Hospitals, doctors' offices and long-term care facilities have a large proportion of patients who are diabetic and require monitoring of their blood glucose levels by healthcare professionals (HCPs). For non-critically ill patients, this is usually carried out using a blood glucose meter and associated disposable test strips. The patient donates a sample of blood which is added to a disposable test strip which is inserted into the blood glucose meter. Inevitably, the process of obtaining the blood sample from the patient may result in spillage of blood onto the blood glucose meter, thereby resulting in potential contamination of the surfaces of the meter. The meter itself is non-disposable and may be used for several thousands of patients. The meter and test strips are typically carried around on a moveable med cart during rounds at the facility. Alternatively, the meter may be kept at a central station.

The blood glucose meters are used on multiple patients, thereby exposing them to bodily fluids such as blood, plasma, saliva, urine and faeces, which may carry infectious agents. Additional sources of chronic infection may also be present in the hospital, including workers, visitors, food, unclean surfaces and solutions. Many hospital and nursing home environments suffer from highly resistant contaminations, such as *C difficile, Pseudomonas*, TB and MRSA, which may be a source of infection. Devices such as glucose monitors must be carefully and thoroughly disinfected between use on multiple patients and after use, to prevent contamination being passed to patients.

The Center for Disease Control (CDC) has recently promulgated much stricter guidelines on disinfection of medical devices, including glucose meters, when used on multiple patients. In many states, these regulations are enforced by inspectors. In particular, these guidelines mandate that the meters be disinfected for requisite periods with EPA-registered pre-wetted wipes. The period of cleaning is described in the claims on the EPA-registered wipes, and the meters must be wrapped in the wipes and kept moist during the cleaning process. Thus, if a disinfection wipe has a 3 minute kill time for *C difficile* and other pathogens, the surface of the blood glucose meter must be kept moist/wet for at least 3 minutes.

The problem for HPCs is having a means of monitoring the period of disinfection and ensuring that the meter they are using is properly disinfected before use on another patient. In a busy hospital with many patients and multiple meters, this is difficult to monitor.

Disinfection periods for difficult-to-kill bacteria may be of several minutes even using bleach wipes (usually the most effective cleaning agent). The HCPs may have multiple patients to visit/monitor blood sugars. Ideally they need a device which will allow disinfection of one blood glucose meter while another is being used. Such a device must allow the minimum of steps, be easy to use, and indicate when a meter has been disinfected.

SUMMARY OF THE INVENTION

According to the present invention, a device (herein also described as a tray or a container) suitable for use in the disinfection of blood glucose meters and other medical devices comprises a tray with a formed cavity in it, such that a blood glucose meter or medical device may be placed and retained in it once the meter has been wrapped in a disinfection wipe.

DESCRIPTION OF PREFERRED EMBODIMENTS

Figure 1:
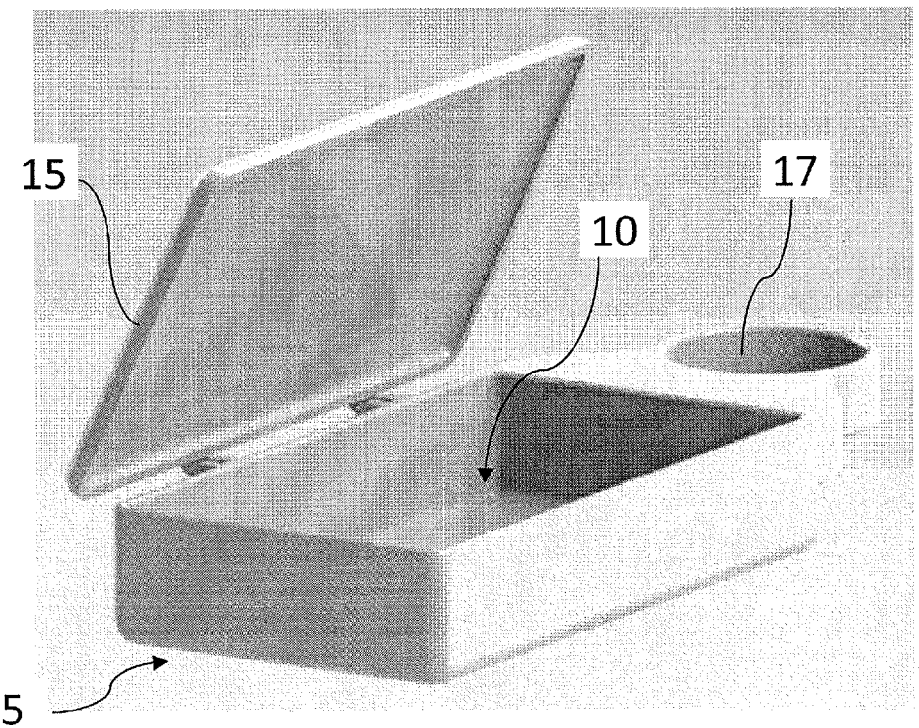
FIG. 1 is a left perspective view of an open disinfecting container according to the present invention.
Figure 2:
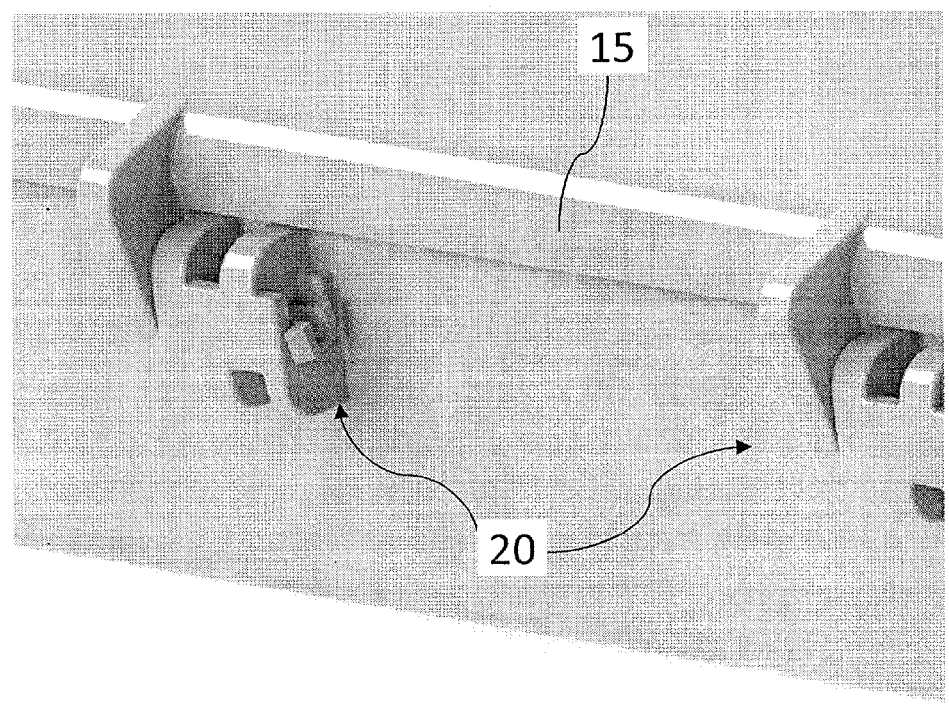
FIG. 2 is a view of the hinge assemblies used with a disinfecting container of FIG. 1.
Figure 3:
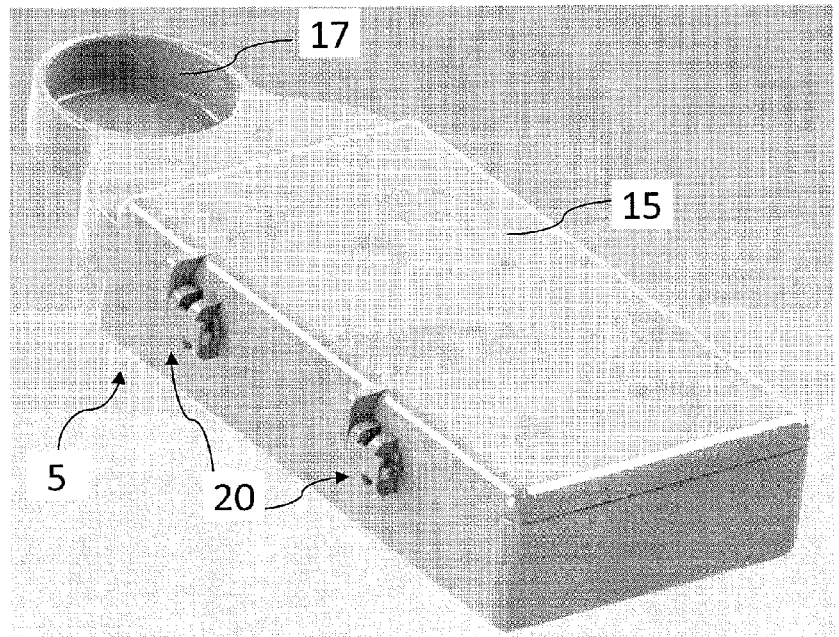
FIG. 3 is a rear perspective view of a closed disinfecting container of FIG. 1.
Figure 4:
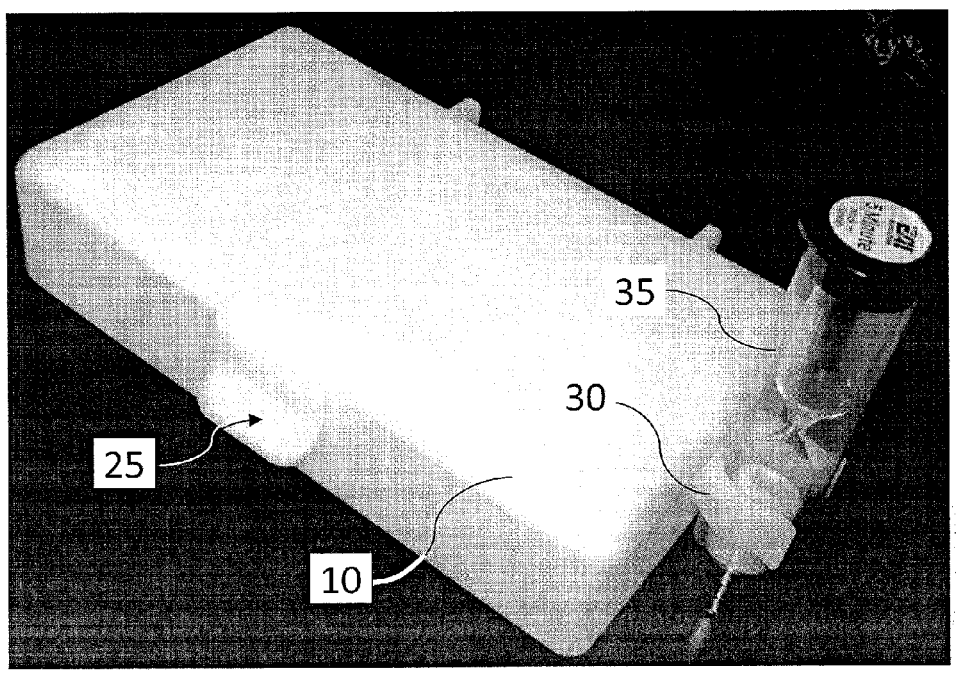
FIG. 4 is a front perspective view of a closed disinfecting container including a timer in accordance with the present invention.
Figure 5:
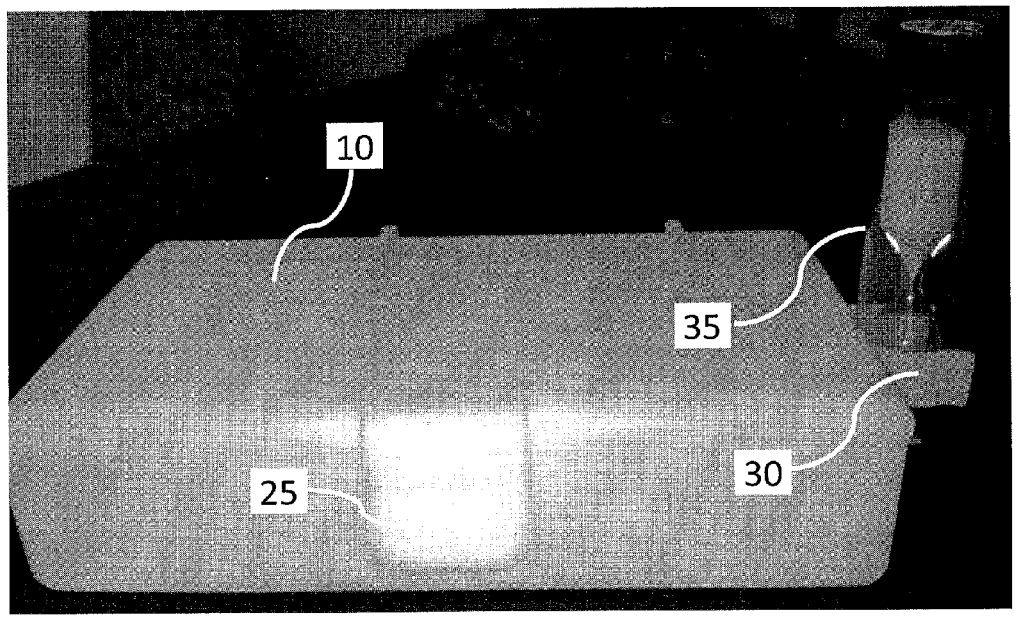
FIG. 5 is a front elevation perspective view of the container of FIG. 4.
Figure 6:
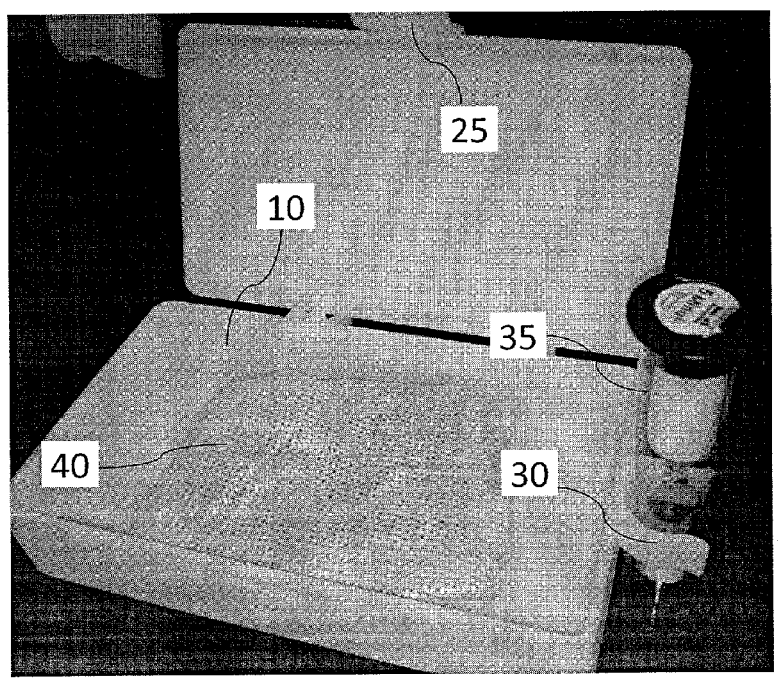
FIG. 6 is a top perspective view of an open disinfecting container with a blood glucose meter wrapped in a disinfection wipe retained therein.

As illustrated in FIGS. 1-6, a container 5 of the invention includes a cavity 10. The cavity may be moulded to fit and retain any type of blood glucose meter. The container 5 may or may not have a lid 15 on it. Preferably, the container will have a lid on it to create a barrier for patient safety, decrease bleach odours, reduce any airborne contamination and prevent drying out of the wipe. The lid may be attached to a container with at least one hinge assembly 20, and preferably two hinge assemblies. Preferably, the hinge assembly 20 is one that enables the lid to be easily removed from the container for ease of cleaning and disinfection. In certain embodiments, the lid 15 includes a latch 25 (FIGS. 4-6).

A container of the subject invention can be of any dimension suitable for retaining a blood glucose meter or other medical device for disinfection. Preferred dimensions for a container are 50-250 mm long, 30-200 mm wide and 10-100 mm high. More preferably, a container of the invention is 145 mm long, 80 mm wide and 35 mm high.

According to the subject invention, any blood glucose meter may be placed into a cavity of a container of the invention. In certain embodiments, a blood glucose meter is wrapped in a disinfection wipe 40 before placement into a cavity (FIG. 6). In related embodiments, it may be advantageous for the disinfection wipe to be compressed around the medical device being disinfected to ensure good contact between the disinfection wipe and the surface of the medical device, thereby ensuring wetting of the medical device surfaces. Good wetting allows the active ingredient from the disinfection wipe to access the surface of the medical device. To achieve this, a compressible layer, such as foam or plastic, may be placed on the inside of the disinfection device, for example, under the lid. Thus when the lid is closed the disinfection wipe is compressed automatically against the medical device. The foam should be anti-bacterial and be of a non-porous nature.

Once the meter has been placed in the cavity, a timing device attached to the tray is started by the HCP who activates the timing device (e.g., pushing a start/stop button on a timer) or the timing device may be started automatically by, for example, a pressure-sensitive pad in the cavity triggered by placing the meter in the cavity. Any form of timer may be used with the container including, for example, electronic and mechanical timers. Electronic or optically activated timers that start once the meter has been placed in the cavity may also be used including, but not limited to, RFID systems or other electronic proximity systems triggered when the meter is placed in the cavity. Alternatively, the timing mechanism may be triggered when the lid is closed. In certain embodiments, the container 5 includes a retainer 17 in which a timer may be placed. HCPs also prefer systems that do not require batteries, so a simple sand timer 35 may also be used, which is attached or clipped 30 to the tray (FIGS. 4-6).

When the pre-set disinfection time (which is given by the nature of the EPA-registered claims on the disinfection wipe) is reached, the timer indicates to the user that disinfection has been completed and the meter is ready to use. This may occur by means of light, a low intensity buzzer or other indicator (e.g. visual or electronic). Achievement of the target disinfection time may also trigger the lid to automatically open. The disinfection period is usually at least 30 seconds, preferably 1 minute and typically at least 3 minutes.

Once disinfection has occurred and the meter is removed, the timing mechanism preferably automatically resets to zero manually or automatically. The cavity in the tray is now ready to accept another meter.

The tray may be provided with two cavities, so that one meter may be used while the other is disinfecting. Alternatively, two trays may be provided, each with its own cavity on each medical cart/trolly. Trays may be mounted horizontally or vertically but, due to the amount of items on a cart, it is usually preferable that such trays are mounted on the side of the cart to allow maximum use of surfaces for other items.

Thus, two or more trays, each with a single cavity, can be used simultaneously to ensure that one meter is undergoing disinfection while the other is being used. Trays with multiple cavities may be used.

Items associated with blood glucose monitoring, such as lancets, finger stickers, alcohol wipes, swabs and disinfection wipes, may be carried in compartments close to or attached to the disinfection trays.

The tray is typically made of a non-porous material that can readily be itself disinfected at regular intervals by bleach wipes, steam disinfection, gamma irradiation or other means. The tray may itself be formed of materials that have anti-bacterial properties.

Record-keeping of disinfection procedures may also be needed, to meet disinfection protocols. These may take the form of written records. In more complex versions of the device, this may be achieved electronically, for example as follows: The disinfection tray automatically records the entry and exit of the meter from the disinfection tray by means of an RFID chip in the meter and a recording device for the RFID chip in the device which records the dwell time of the meter in the device and the serial number of the meter. Alternatively, this may also be linked with the closing and opening of the lid on the device. Electronic disinfection records may therefore be kept for each disinfection device.

The following Example illustrates the invention, and in particular a Microdot® Bleach Wipe Disinfection Tray/Container System with Timer.

EXAMPLE

In this Example, a Microdot® blood glucose meter (Cambridge Sensors USA, LLC) is used with a Microdot® Bleach disinfection wipe available from the same company.

The Microdot® Bleach Wipe disinfection container system is designed to provide health care facilities a turnkey disinfection process and protocol for disinfecting Point-of-Care equipment used in multi-patient settings like hospitals, nursing homes, clinics and physician offices where regulations demand proper disinfection of devices shared between patients. The Microdot® Bleach Wipe disinfection system utilizes a PET moulded container system that allows devices such as blood glucose meters to be wrapped in the Microdot® Bleach wipe and placed inside a fully enclosed container with a mechanical hinged lid. Attached to the container is a 3 or 5 minute timer that is calibrated to match the appropriate dwell time of Microdot® Bleach wipe.

The Disinfection System comprises a Microdot® Disinfection container, 3 or 5 minute timer, Microdot® Bleach Wipe Disinfection System Policy & Procedure Manual. The Manual provides:
  Over View and System Components
  Microdot® Bleach Wipe Kill Claims and Dwell (EPA #69687-1-88459)
  MSDS (Material Safety Data Sheet)—Microdot® Bleach Wipe
  Efficacy Studies for EPA registration
  In-Service Training Guide
  Illustrated procedure of proper device wipe wrap to maintain appropriate wet time with timer
  Quick Reference Guide: line art step by step
  User return demonstrate competency test of proper disinfection process
  In-Service sign-in sheet

I claim:

1. A container comprising a cavity shaped to receive a medical device, wherein said container further comprises a timer, wherein the timer comprises an activator and an indicator to indicate when a predetermined period has elapsed, and a layer to conform about the medical device.

2. The container according to claim 1, wherein the predetermined period is initiated on placing the device in the cavity.

3. The container according to claim 1, which additionally comprises a lid over the cavity.

4. The container according to claim 3, wherein the lid is hinged.

5. The container according to claim 3, wherein the predetermined period is initiated when the lid is closed after placing the device in the cavity.

6. The container according to claim 3, wherein the layer is located under the lid and the layer is a compressible layer.

7. The container according to claim 1, wherein the container is 50-250 mm long, 30-200 mm wide and 10-100 mm high.

8. The container according to claim 6, wherein the container is 145 mm long, 80 mm wide and 35 mm high.

9. The container according to claim 1, wherein the timer is selected from an electronic or mechanical timer.

10. The container according to claim 1, wherein the timer is a sand timer.

11. The container according to claim 1, wherein the layer is a compressible layer.

12. The container according to claim 11, wherein the compressible layer is foam or plastic.

13. A method for disinfecting a medical device, which comprises wrapping the device in a disinfectant wipe, placing the wrapped device in a cavity of a container, wherein the container comprises a timer, wherein the timer comprises an activator and an indicator to indicate when a predetermined period has elapsed, wherein said predetermined period is sufficient to disinfect the device.

14. The method according to claim 13, wherein the predetermined period is initiated on placing the device in the cavity.

15. The method according to claim 13, wherein the container additionally comprises a lid over the cavity.

16. The method according to claim 15, wherein the lid is hinged.

17. The method according to claim 15, wherein the predetermined period is initiated when the lid is closed after placing the device in the cavity.

18. The method according to claim 13, wherein the predetermined period is at least 1 minute.

19. The method according to claim 13, wherein the medical device is a glucose monitor.

20. The method according to claim 13, wherein the container is 50-250 mm long, 30-200 mm wide and 10-100 mm high.

21. The method according to claim 17, wherein the container is 145 mm long, 80 mm wide and 35 mm high.

22. The method according to claim 13, wherein the timer is selected from an electronic or mechanical timer.

23. The method according to claim 13, wherein the time is a sand timer.

24. A container comprising a cavity shaped to receive a medical device, wherein said container further comprises a timer, wherein the timer comprises an activator and an indicator to indicate when a predetermined period has elapsed, and wherein the timer is a sand timer.

* * * * *

UNITED STATES PATENT AND TRADEMARK OFFICE
CERTIFICATE OF CORRECTION

Page 1 of 1

| | |
|---|---|
| PATENT NO. | : 9,022,247 B2 |
| APPLICATION NO. | : 13/661699 |
| DATED | : May 5, 2015 |
| INVENTOR(S) | : Engimann |

It is certified that error appears in the above-identified patent and that said Letters Patent is hereby corrected as shown below:

In the Claims

Column 4, Claim 8
Line 60, "according to claim 6" should read --according to claim 7--.

Column 6, Claim 21
Line 8, "according to claim 17" should read --according to claim 20--.

Signed and Sealed this
Fifteenth Day of September, 2015

Michelle K. Lee
*Director of the United States Patent and Trademark Office*